United States Patent [19]
Sternberg et al.

[11] Patent Number: 5,880,145
[45] Date of Patent: Mar. 9, 1999

[54] CLASS OF BENZOPORPHYRIN DERIVATIVE PHOTOACTIVE COMPOUNDS

[75] Inventors: Ethan D. Sternberg; David Dolphin; Andrew Tovey; Anna M. Richter; Julia G. Levy, all of Vancouver, Canada

[73] Assignee: The University of British Columbia, Vancouver, Canada

[21] Appl. No.: 918,840

[22] Filed: Aug. 26, 1997

Related U.S. Application Data

[63] Continuation-in-part of Ser. No. 852,326, May 7, 1997.
[51] Int. Cl.[6] .................. A61K 31/40; C07D 487/22
[52] U.S. Cl. ................. 514/410; 540/145; 514/6
[58] Field of Search ................ 540/145; 514/185, 514/410

[56] References Cited

U.S. PATENT DOCUMENTS

| | | | |
|---|---|---|---|
| 4,883,790 | 11/1989 | Levy et al. | 540/145 |
| 4,920,143 | 4/1990 | Levy et al. | 540/145 |
| 5,095,030 | 3/1992 | Levy | 540/145 |
| 5,171,749 | 12/1992 | Levy et al. | 514/410 |
| 5,283,255 | 2/1994 | Levy et al. | 514/410 |
| 5,399,583 | 3/1995 | Levy et al. | 514/410 |

*Primary Examiner*—Mukund J. Shah
*Assistant Examiner*—Pavanaram K. Sripada
*Attorney, Agent, or Firm*—Morrison & Foerster LLP

[57] ABSTRACT

New compounds expanding the repertoire of compounds useful in photodynamic therapy are described. Monohydrobenzoporphyrins can be obtained in the triacid form or as esters with heteroatom-substituted alcohols, or as amides.

43 Claims, 5 Drawing Sheets

BPD-DA

BPD-DB

BPD-MA

BPD-MB

CLASS OF BENZOPORPHYRIN DERIVATIVE PHOTOACTIVE COMPOUNDS

This application is a continuation-in-part of U.S. Ser. No. 08/852,326, filed 7 May 1997, the contents of which are incorporated herein by reference in their entirety.

TECHNICAL FIELD

The field of invention is the design and synthesis of compounds useful in photodynamic therapy and related applications of photoactive compound technology. In particular, the invention is directed to methods to prepare a class of benzoporphyrin derivatives with controlled derivatization at three of four carboxyl substituents. The invention also relates to the resulting compounds as members of this class.

BACKGROUND ART

Photodynamic therapy (PDT) generally involves the administration of compounds that are capable of absorbing light, typically in the visible range, but also in the near ultraviolet, followed by irradiation of locations in the subject for which a toxic, modifying or inhibitory effect is desired. PDT was initially developed using hematoporphyrin and related compounds in the treatment of tumors, as it appeared that these compounds would "home" to locations containing rapidly dividing cells. The tumor could then be irradiated with light absorbed by the hematoporphyrin and destruction of the surrounding tissue resulted. PDT has since been shown to be useful for treatment of atherosclerotic plaques, restenosis, infections in the blood stream, rheumatoid arthritis, psoriasis and in the treatment of ocular conditions not necessarily limited to tumors.

U.S. Pat. No. 5,171,749 and patents issuing on related applications, U.S. Pat. Nos. 5,283,255; 5,399,583; 4,883,790; 4,920,143; and 5,095,030; all of which are incorporated herein by reference, describe and claim a class of photoactive compounds useful in PDT designated the monohydrobenzoporphyrins, or "BPDs." This class is obtained by Diels-Alder reaction of a mono- or disubstituted alkyne with protoporphyrin-IX and the resultant compounds can further be isomerized, reduced, and/or derivatized to obtain a large class of BPDs. As disclosed in these patents, a particularly useful subclass of this group results from hydrolysis or partial hydrolysis of the ester groups of the 2-carboxylethyl side-chains on rings C and D. Esterification as protection of these groups during the Diels-Alder reaction results in initial products which contain 2-carbalkoxyethyl groups. It was found that facile hydrolysis of these esters could readily be conducted, leaving any carbalkoxy groups associated with the Diels-Alder product obtained from a dicarbalkoxyalkyne virtually completely unhydrolyzed. This resulted in four species of compounds, BPD-MA, BPD-MB, BPD-DA and BPD-DB as depicted in FIG. 1; this figure taken from U.S. Pat. No. 5,171,749. In this depiction, $R^1$ and $R^2$ are carbalkoxy groups, typically carbomethoxy or carboethoxy, and R is alkyl (1-6C).

BPD-MA was found to have particularly useful properties for PDT and is currently in clinical development. However, there remains a need for additional specific forms of photoactive agents which expand the repertoire of photoactive compounds for the variety of indications to which PDT is applied, as noted above. The present invention provides a process for the preparation of hitherto undisclosed and inaccessible members of a class related to that of the compounds disclosed in the above-referenced patents; wherein specific controlled derivatization at three of the carboxyl substituents provides a new set of photoactive compounds with desirable properties. Included are the "triacid" form as well as a particularly useful homotriester wherein the triacid is esterified at all three carboxyl groups with ethylene glycol.

DISCLOSURE OF THE INVENTION

The methods and compounds of the invention provide particularly useful new additions to the repertoire of compounds useful in photodynamic therapy as well as means to expand this repertoire in a methodical fashion. The methods of the invention take advantage of the ability to adjust hydrolysis conditions so as to obtain the previously undisclosed triacid form of the monohydrobenzoporphyrin class of photoactive compounds, and the ability to derivatize the resulting three carboxyl groups in a controlled manner.

Thus, in one aspect the invention is directed to a compound of the formula

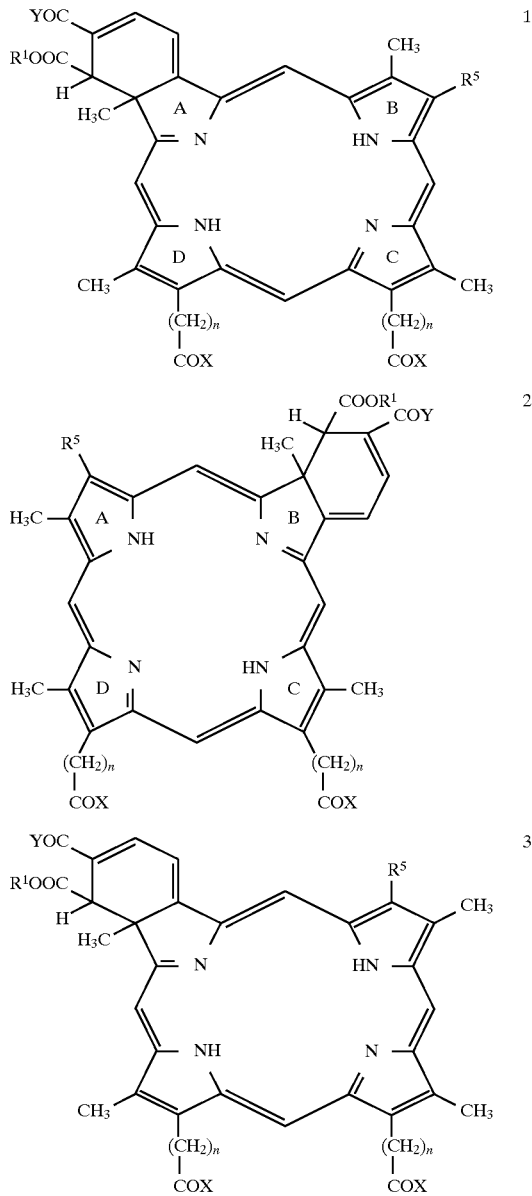

-continued

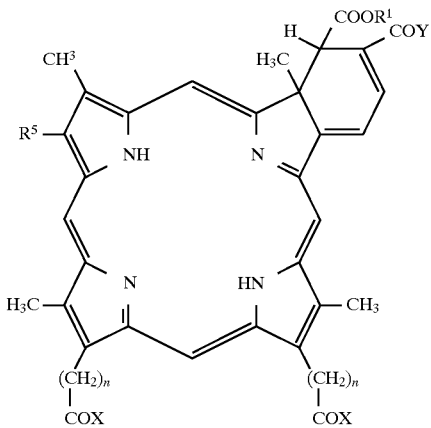

4

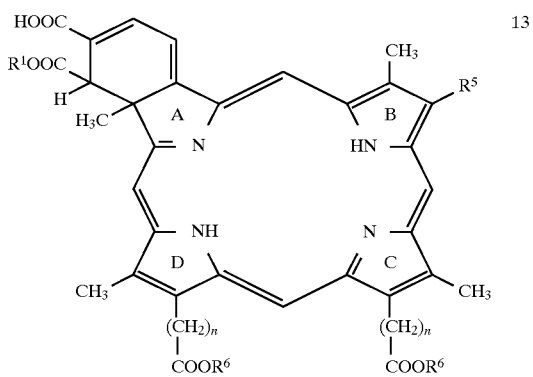

13 including the salts and the metallated and/or labeled and/or conjugated forms of these compounds. It will be noted that compounds 1 and 2 differ only in the location of the Diels-Alder substituent in the A versus B ring. Two such products result because protoporphyrin IX, the starting material for preparation of compounds 1 and 2 is not symmetrical in substitution in these rings. On the other hand, the compound of formula 3 results from similar Diels-Alder addition to protoporphyrin III; the compound of formula 4 from Diels-Alder addition to protoporphyrin XIII. As these protoporphyrins are symmetrically substituted, only one product results in each case.

In formulas 1–4, $R^1$ represents alkyl (1-6C), Y represents OH (including the salt forms), $NR^2_2$ or $NHR^2$ wherein each $R^2$ is independently H or a substituted or unsubstituted hydrocarbon radical of 1-10C, or wherein both $R^2$ taken together provide a cyclic or multicyclic amine of 1-20C, or $OR^3$ wherein $R^3$ is a hydrocarbon radical of 1-10C which must be substituted with at least one heteroatom-containing substituent. In formulas 1–4, X is defined as Y is defined, but in addition can include embodiments wherein X is $OR^4$ wherein $R^4$ is hydrocarbon radical (unsubstituted, 1-10C). "n" is an integer of 0–6, and is preferably 2. $R^5$ is vinyl or a derivative thereof.

The invention is also directed to methods to make the compounds of formulas 1–4 wherein X and Y are OH (or the corresponding salts) by treating a more completely esterified form of the compound of appropriate formulas 1–4, dissolved in an appropriate solvent, with base under an oxidatively inert atmosphere for a time sufficient to deesterify sufficient carboxyl groups to obtain the triacid form, and recovering the triacid from the reaction mixture.

Included in the invention are compounds of formulas 1–4 wherein all of X and Y are $OCH_2CH_2OH$. These compounds, like the triacids, are useful photoactive compounds for use in various applications of photodynamic therapy.

Also included in the invention as a preferred embodiment are the compounds of the formulas

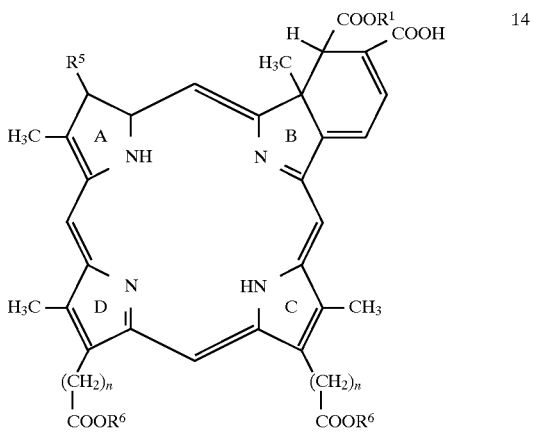

14

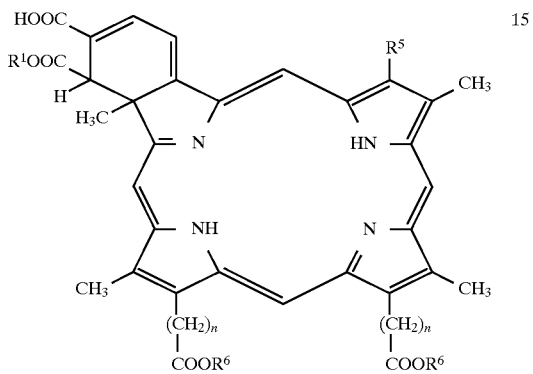

15 or

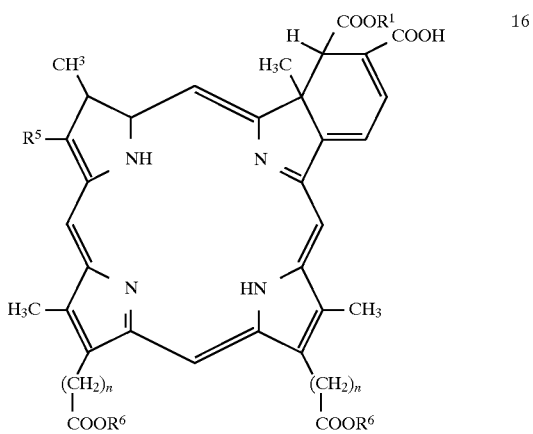

16 wherein $R^1$ and $R^5$ are defined as above and $R^6$ is lower alkyl (1-4C) and pharmaceutical compositions containing these compounds as well a methods to perform PDT using them. Particularly preferred are these compounds wherein $R^5$ is vinyl and $R^1$ is lower alkyl (1-4C).

MODES OF CARRYING OUT THE INVENTION

Figure 1:
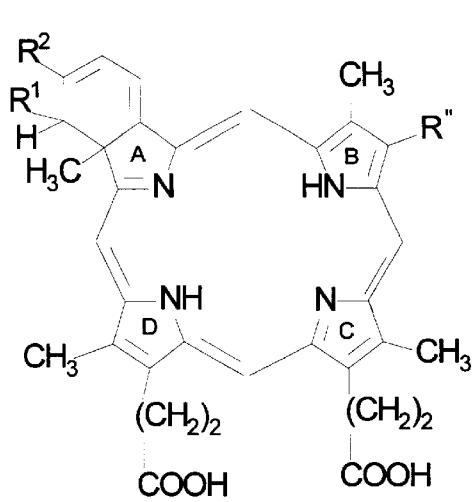
FIG. 1 shows the compounds of the prior art, BPD-MA, BPD-MB, BPD-DA and BPD-DB.
Figure 1:
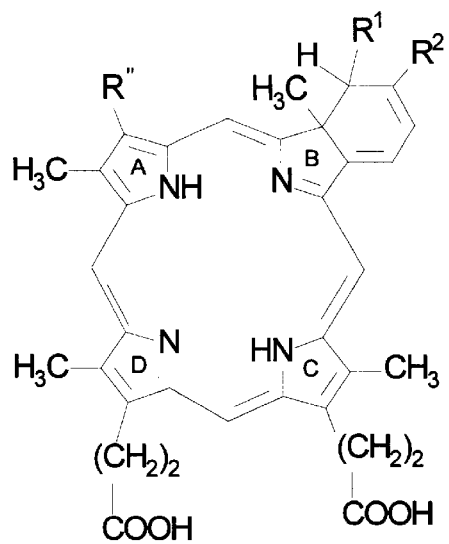
Figure 1:
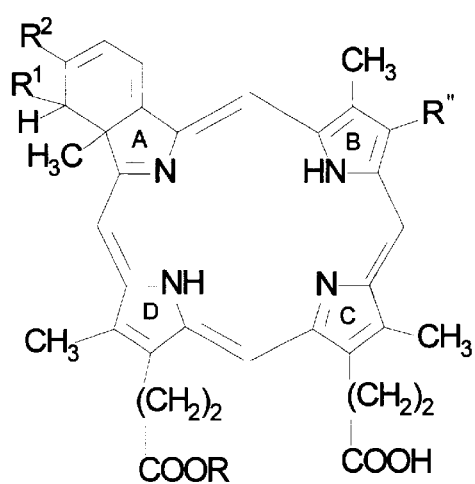
Figure 1:
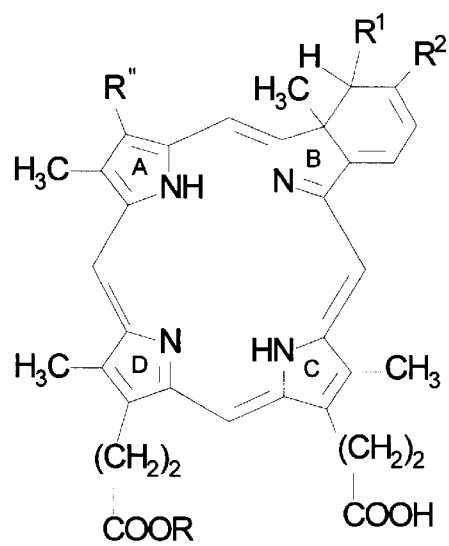

The compounds of formulas 1–4 of the invention are analogous to those set forth in U.S. Pat. No. 5,171,749 and its parents, U.S. Pat. Nos. 5,283,255; 5,399,583; 4,883,790; 4,920,143; and 5,095,030. The compounds of the invention differ from those set forth in these patents by virtue of derivatization at the three carboxyl groups shown as "COY" and "COX" in these formulas. Formation of these compounds has been precluded by the difficulty in hydrolyzing the carbalkoxy group at the position occupied by "COY." The present invention provides access to this carbalkoxy and permits the synthesis of a variety of photoactive compounds that were hitherto inaccessible.

To simplify the discussion, the substituent "COY" will be referred to as the "vinyl carboxyl" regardless of the embodiment of Y in the compound being discussed. The groups designated "COX" will be referred to as the "propionic carboxyl" again regardless of the embodiment of X or n in any particular compound.

The present inventors have found that by suitably adjusting the conditions for hydrolysis, the vinyl carboxyl group can be accessed. Although the propionic carboxyl groups are readily manipulated by deesterification, reesterification, or further derivatization, the vinyl carboxyl in the form of an alkyl ester is more resistant to hydrolysis and, indeed, hydrolysis that succeeds with respect to this group must be conducted under conditions that prevent the oxidation or destruction of the molecule.

The ability to access the vinyl carboxyl group has important consequences. First, the triacid compound, as thus formed, itself is an important new photoactive agent. Second, because the propionic carboxyl groups are the most reactive, they can readily be reesterified for protection and the vinyl carboxyl then activated for further substitution. Thus, a series of compounds can be obtained wherein the propionic carboxyl groups are either in the form of free acids and salts or simple esters or amides or acyl hydrazides, and wherein the vinyl carboxyl is a free acid or salt or is derivatized as a complex ester or an amide or acyl hydrazide.

The compounds of the invention exist in the form of optical isomers. Regardless of whether separation into individual optical isomers is effected, the compounds obtained by forming derivatives at the vinyl carboxyl themselves are useful as photoactive agents. The availability of additional compounds in the repertoire of photoactive agents permits adjustment of protocols to fit particular indications and individuals.

The accessibility of the vinyl carboxyl also permits formation of photoactive agents wherein all three carboxyl groups (the vinyl carboxyl and the propionic carboxyls) are identically derivatized, thus providing still additional members to the repertoire of photoactive compounds. Finally, it will be apparent that a variety of combinations of substitutions at the three relevant carboxyl groups provides a range of compounds which range is enhanced by the variety obtainable at $R^5$ by virtue of derivatization of the vinyl substituent.

Thus, even without adjusting the conditions so that only one of the propionic carboxyls is reacted, and aside from the potential for variety at $R^5$, available combinations include those shown in Table 1.

TABLE 1

|  | vinyl carboxyl Y= | propionic carboxyl X= |
|---|---|---|
| X-1 | —OH | —OH |
| X-2 | —OH | —OR$^4$ |
| X-3 | —OH | —OR$^3$ |
| X-4 | —OH | —NR$^2_2$ or —NHNR$^2_2$ |
| Y-1 | —OR$^3$ | —OH |
| Y-2 | —OR$^3$ | —OR$^4$ |
| Y-3 | —OR$^3$ | —OR$^3$ |
| Y-4 | —OR$^3$ | —NR$^2_2$ or —NHNR$^2_2$ |
| Z-1 | —NR$^2_2$ or —NHNR$^2_2$ | —OH |
| Z-2 | —NR$^2_2$ or —NHNR$^2_2$ | —OR$^4$ |
| Z-3 | —NR$^2_2$ or —NHNR$^2_2$ | —OR$^3$ |
| Z-4 | —NR$^2_2$ or —NHNR$^2_2$ | —NR$^2_2$ or —NHNR$^2_2$ | wherein OH represents the free acid or salt, depending on pH.

To obtain the compounds of Group X-1, the Diels-Alder product or any more highly esterified form of the compounds of this group with respect to the vinyl and propionic carboxyls is hydrolyzed under the conditions described herein to obtain the triacid form. To obtain the compounds of Groups X-2, X-3 and X-4, the propionic carboxyls are reesterified or amidated using standard methods as they are greatly more reactive than the vinyl carboxyl.

Using this method, a particularly preferred compound, designated "B3" herein was prepared, as set forth in Example 3 hereinbelow.

In order to obtain the compounds of Group Y-3, the three carboxyl groups of the triacid are first activated and then reacted with the alcohol corresponding to —OR$^3$. For the remaining members of Group Y, as the propionic carboxyl groups can readily be manipulated without disturbing the vinyl carboxyl, the original ester comprising —OR$^3$ can be reacted in favor of forming the free acid, the unsubstituted hydrocarbon ester (—OR$^4$) or the amide.

The amides of Groups Z-2 and Z-3 are most conveniently obtained by first esterifying the propionic carboxyls (wherein X=—OR$^4$ or —OR$^3$) followed by activation of the vinyl carboxyl and subsequent amidation. To obtain the compounds of Group Z-1, these ester groups are simply removed by straightforward hydrolysis. The compounds of Group Z-4 are obtained from those of Group Z-2 by hydrolysis of the ester group on the propionic carboxyls followed by their activation and conversion to an amide or hydrazide. Alternatively, the compounds of Group Z-4 can be obtained directly from the triacid as shown in Reaction Scheme 3 below.

Illustrative reaction schemes for formation of these compounds are set forth below.

Reaction Scheme 1 shows the conversion of the triacid intermediate, obtained by the method of the invention, to the compounds of Group X-2 or X-3 through simple esterification under standard conditions of the propionic carboxyls. These standard conditions include treatment of the triacid intermediate with the appropriate alcohol in the presence of an acid, such as sulfuric, hydrochloric, triflic, or other suitable acid.

Reaction Scheme 1

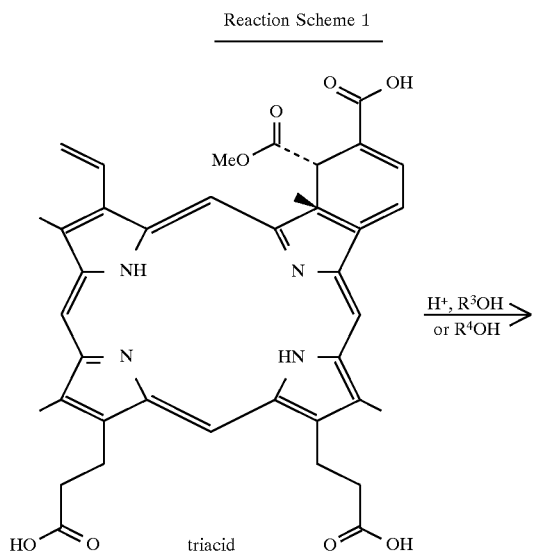

triacid

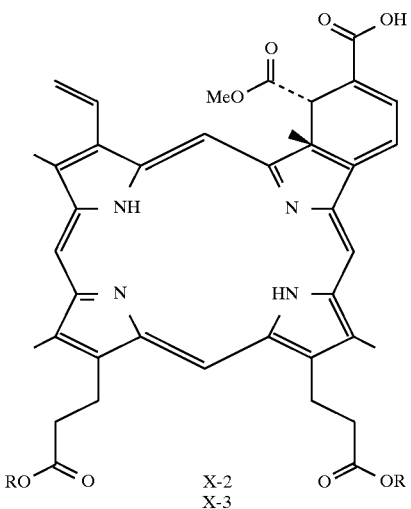

X-2
X-3 wherein R is $R^3$ or $R^4$.

The illustrated conversion shows the Diels-Alder substituent in the B ring derived from protoporphyrin IX, i.e., the compound of formula 2, and a vinyl substituent at $R^5$, however, Reaction Scheme 1 is general to compounds of the invention and is merely illustrative as shown. Other embodiments of $R^5$ and compounds of formulas 1, 3 or 4 could equally have been used for illustration.

Particularly preferred products of this reaction scheme are the compounds of formulas 13–16 set forth above. These compounds can be formulated into therapeutic compositions for use in PDT.

Reaction Scheme 2 shows conversion of the triacid intermediate to compounds of Groups Z-1, Z-2 or Z-3.

Reaction Scheme 2

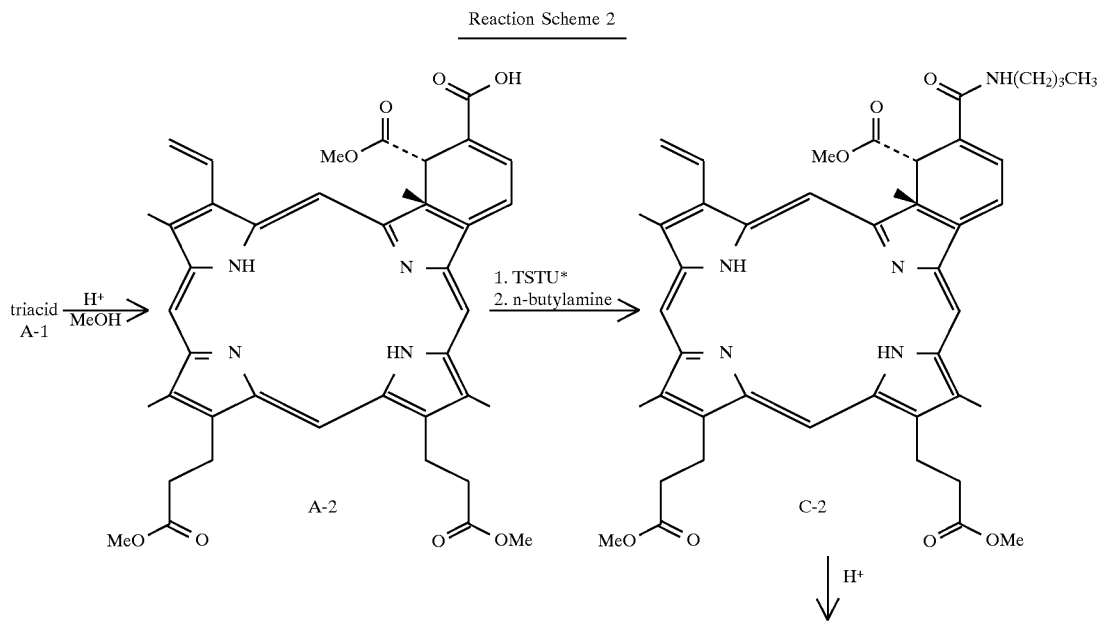

-continued
Reaction Scheme 2

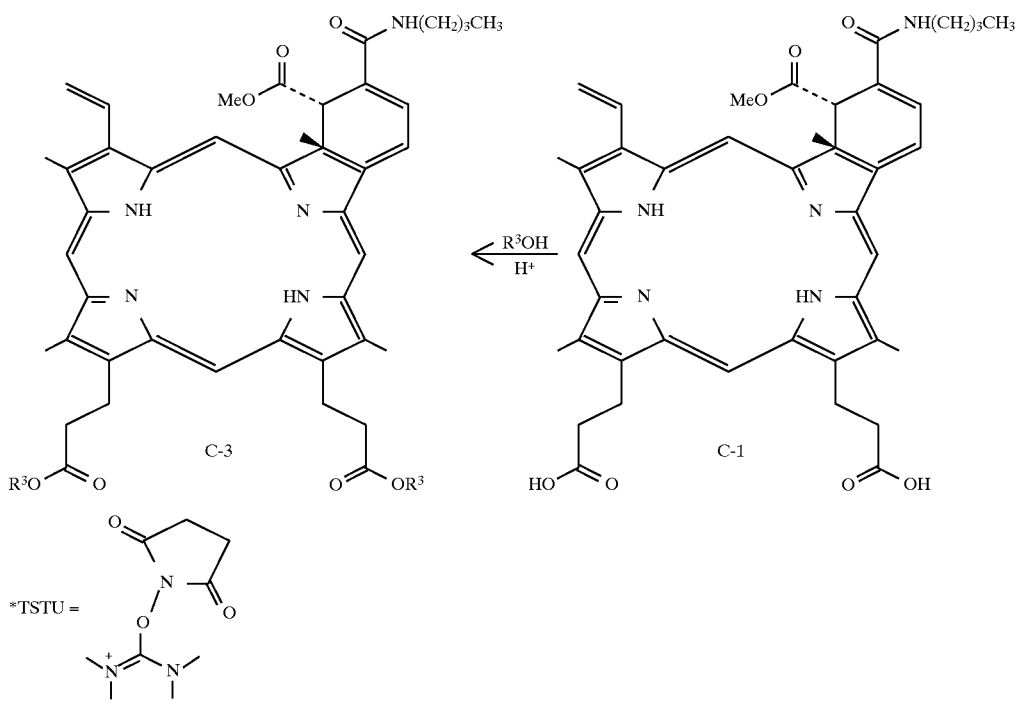

As shown in Reaction Scheme 2, the triacid form is first conveniently esterified at the propionic carboxyls with an unsubstituted hydrocarbon radical alcohol (MeOH, for example) to protect these positions; the vinyl carboxyl is then activated with TSTU and then amidated using N-butyl amine (for illustrative purposes). Of course, a wide variety of primary or secondary amines or hydrazines could have been used. The resultant of this reaction is of the Group Z-2; compounds of the Group Z-1 are readily obtainable by acid hydrolysis of the propionic carboxyls and more complex esters can then be formed at these positions to obtain the compounds of Group Z-3.

Reaction Scheme 3 illustrates the formation of compounds of Group Z-4 wherein the triacid form is activated with TSTU without protecting the propionic carboxyls and amidated at all three positions.

Reaction Scheme 3

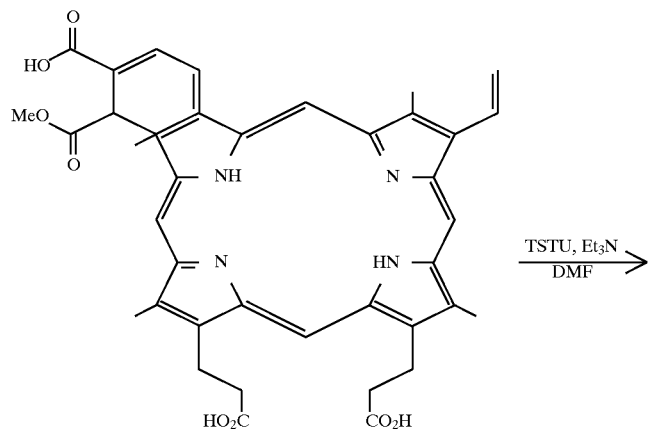

-continued
Reaction Scheme 3

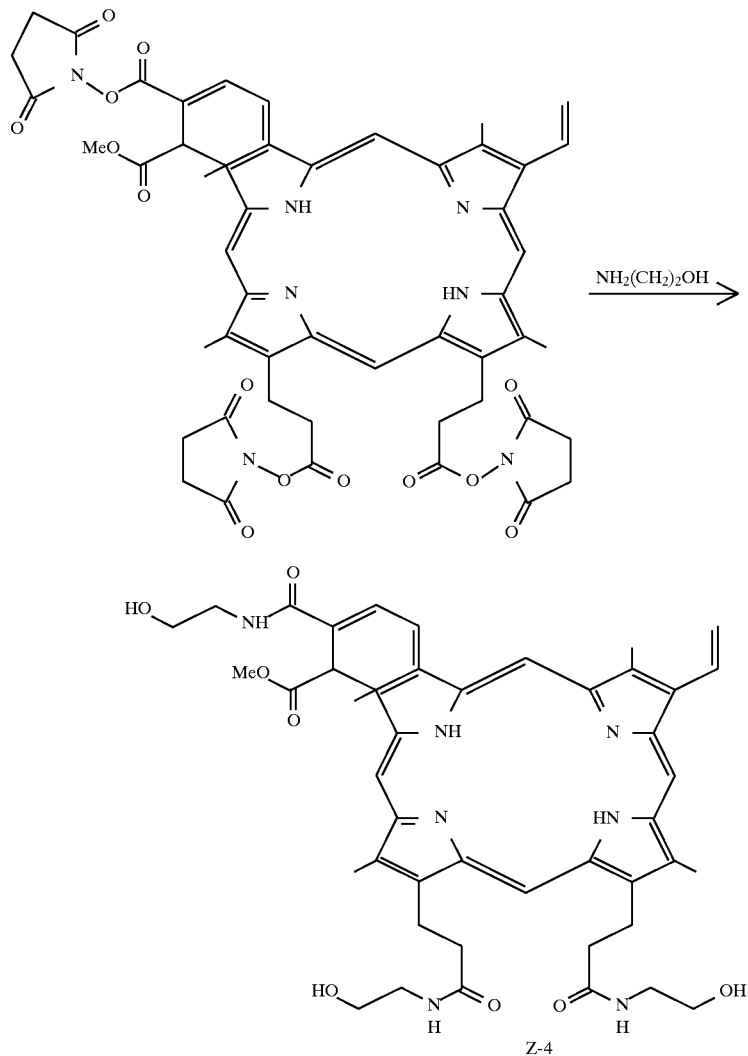

As shown, complex amides can be formed in this manner; a wide variety of amides can thus be obtained.

If it is desired to obtain different amide substituents at the propionic carboxyls as compared to the vinyl carboxyl, the compound representative of Z-1 or Z-2 in Reaction Scheme 2 is first obtained and the resulting carboxyl groups activated to obtain the desired amides.

To obtain the compounds of Groups Y-1 through Y-4, the desired ester at the vinyl carboxyl is first obtained as shown in Reaction Scheme 4, to yield the compounds of Group Y-3.

Reaction Scheme 4
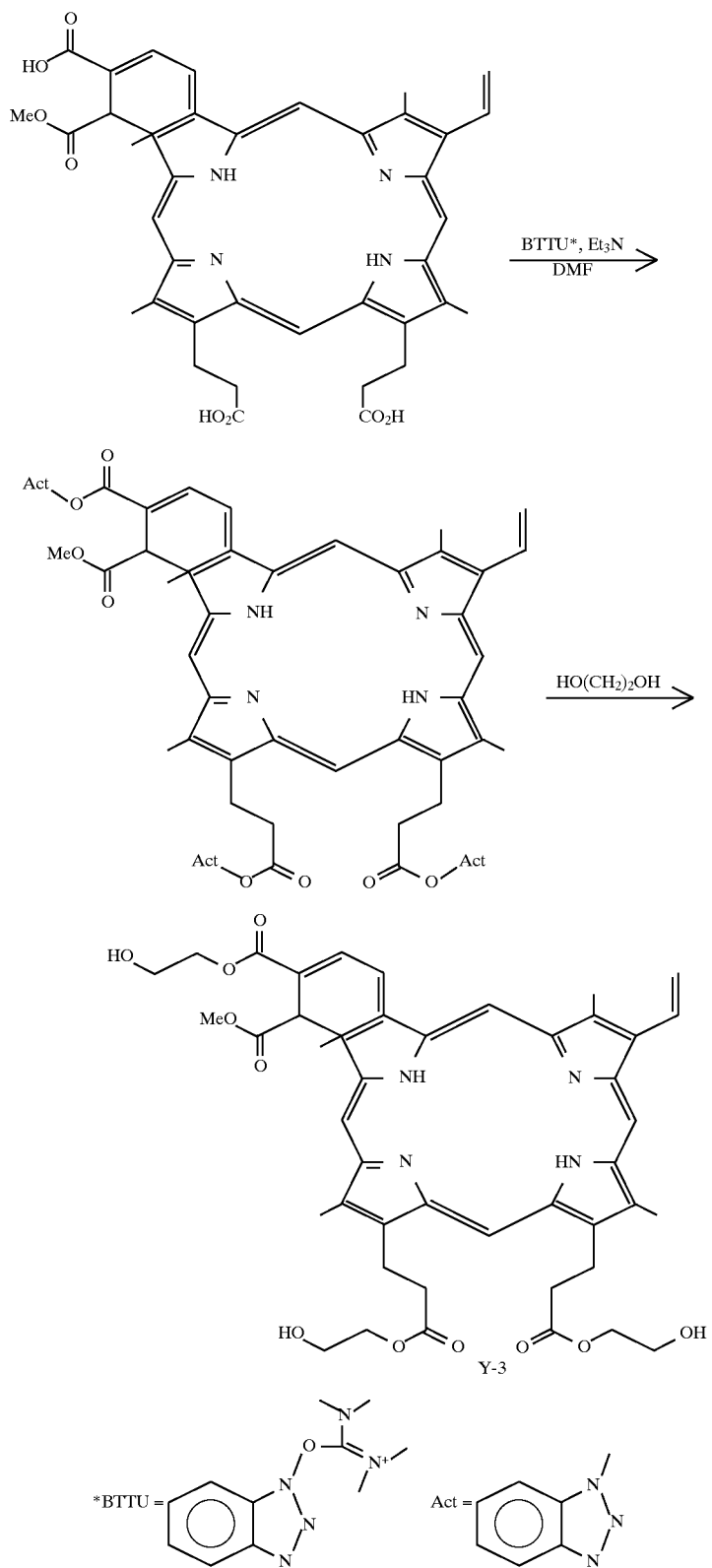

The resulting triester can then be manipulated in a manner analogous to the Diels-Alder product as described in the BPD patents referenced above; the propionic carboxyl esters are readily hydrolyzed in acid to obtain the compounds of Group Y-1 and the acid can be manipulated as above-described to obtain the compounds of Groups Y-2 and Y-4.

As set forth above, the methods of the invention, and in particular, the availability of the triacid forms of the BPD-type compounds, particularly in conjunction with the availability of the vinyl group at $R^5$ for derivatization, provide the means to synthesize large number of related photoactive agents. Such synthesis could be planned and conducted in a random or systematic fashion to obtain large numbers of compounds which, in this sense, are considered combinatorial libraries.

The substituents on the BPDs of the invention are described in terms of the characterization of $R^1$–$R^5$. The terminology can be further defined as follows:

As used herein, the term "alkyl" refers to a saturated straight or branched chain hydrocarbon which may, if it contains a sufficient number of carbon atoms, be cyclic or contain a cyclic portion. Typical examples are methyl, ethyl, t-butyl, cyclohexyl, and the like.

A "hydrocarbon radical" refers to a monovalent substituent containing only carbon and hydrogen which may be straight or branched chain, saturated or unsaturated, aromatic or nonaromatic or both, and can be cyclic or noncyclic. Thus, a hydrocarbon radical of 1-10C could include cyclopentylethyl, 2-pentenyl, 3-butynyl, 2,4-dimethylhexyl, and the like.

In some substituents, e.g., $R^2$ and $R^3$, the hydrocarbon radical may be substituted with a heteroatom-containing substituent. Such substituents include —OR, —NR$_2$, —SR, —COOR, —CONR$_2$, —OOCR, —NRCOR, —SOR, —SO$_2$R, —SO$_3$R, halo, —CN, and the like, wherein R is H or alkyl (1-6C), as well as heterocyclic radicals, including cyclic amines such as pyridyl, pyrimidyl, thiazolyl, quinolyl, and so forth. Thus, the heteroatom-containing substituent may include single ring or fused ring systems and may contain additional heteroatoms.

Embodiments wherein X or Y is —NR$^2$$_2$ or —NHNR$^2$$_2$ include embodiments wherein each $R^2$ is independently H, alkyl, alkenyl, cyclic alkyl or an unsaturated cyclic hydrocarbon radical or aryl substituents such as phenyl or substituted phenyl. However, NR$^2$$_2$ or —NHNR$^2$$_2$ can also be more complex and can comprise various cyclic amines as direct substituents at the nitrogen, or the specified nitrogen can itself be a member of the ring. Such cyclic amines include: pyrrolyl, isopyrrolyl, pyridyl, pyrazolyl, indolyl, isoindolyl, imidazolyl, isoimidazolyl, triazolyl, furazanyl, isoxazolyl, oxazolyl, thiazolyl, isothiazolyl, oxadiazolyl, oxatriazolyl, dioxazolyl, pyridinyl, pyridazinyl, pyrimidinyl, pyrazinyl, piperazinyl, indolyzinyl, pyrrolidinyl, triazinyl, oxazinyl, isoxazinyl, oxathiazinyl, oxadiazinyl, morpholinyl, azepinyl, diazepinyl, indenyl, isoindenyl, indolenyl, isobenzazolyl, pyrano-pyrrolyl, indazolyl, isoindazolyl, indoxazinyl, benzoxazolyl, benzopyronyl, quinolinyl, isoquinolinyl, benzodiazinyl, quinolyl, isoquinolyl, quinazolinyl, quinolizinyl, quinoxalinyl, naphthyridinyl, pyrido-pyridinyl, benzoxazinyl, benzisoxazinyl, purinyl, phthalazinyl, naphthyridinyl, and pteridinyl.

Cyclic amines, when monovalent, also fall under the definition of hydrocarbon radicals (1-10C) substituted with a heteroatom-containing substituent, as set forth in the definition of $R^3$. Also included are ring systems such as furyl, thienyl, pyranyl, dioxinyl, oxepinyl, thiepinyl, benzofuranyl, isobenzofuranyl, thionaphthenyl, isothionaphthenyl, benzothenyl, benzopyranyl, coumarinyl, and cinnolinyl.

Suitable unsubstituted hydrocarbon radicals of 1-10C as embodied in $R^4$ and included in $R^2$ include, for example, methyl, ethyl, propyl, butyl, hexyl, cyclopentadienyl, phenyl, chromenyl, anthanyl, naphthyl, or benzyl. These embodiments can also be included in the definition of $R^3$ provided they are substituted with a heteroatom-containing substituent as set forth above.

To form the amides, the relevant carboxylic acid groups are activated, for example, to obtain the acyl halides, or using milder conditions such as the illustrated tetramethyl uronium based agents, carbodiimides or activated esters, such as p-nitrophenyl. The activated carboxyl is then treated with a suitable amine or hydrazine.

In the compounds of the invention, $R^5$ is preferably vinyl, but may also be a derivative thereof. The vinyl group in ring A or B is readily derivatized to other embodiments of $R^5$ by addition or oxidation. The addition or oxidation products can be further substituted if the added substituents are functional as leaving groups, for example, —Br may be substituted by —OH, —OR", —NH$_2$, —NHR", or —NR$_2$", etc., where R" is a hydrocarbon radical. For instance, one of the added substituents may be hydrogen and the other halo, hydroxy, lower alkoxy, amino, or an amide, sulfhydryl or an organosulfide or an additional hydrogen. The compounds of the invention include various groups as $R^5$ including substituents which provide additional porphyrin or porphyrin-related ring systems.

Thus, $R^5$ may be vinyl, —CHOR', —CHO, —COOR', —CH(OR')CH$_3$, —CH(OR')CH$_2$OR', —CH(SR')CH$_3$, —CH(NR')$_2$CH$_3$, —CH(CN)CH$_3$, —CH(COOR')CH$_3$, —CH(OOCR')CH$_3$, —CH(NR'COR')CH$_3$, —CH(CONR'$_2$)CH$_3$, —CH(halo)CH$_3$, or —CH(halo)CH$_2$(halo) wherein R' is H, or a hydrocarbon radical (1-6C) optionally substituted with a heteroatom substituent or wherein $R^5$ is an organic group of less than 12C resulting from direct or indirect derivatization of the vinyl group, or wherein $R^5$ is a group containing 1–3 tetrapyrrole-type nuclei.

It will be noted that the compounds of the invention may contain one or more chiral centers and thus exist in enantiomeric or diasteriomeric forms. Formulas 1–4, as representative of the compounds of the invention, thus represent optically pure enantiomers or diesteriomers or may be racemic mixtures or mixtures of diesteriomers as the case may be.

If desired, the compounds of the invention can be prepared in metallated forms by treating the tetrapyrrole type nucleus with an appropriate ion such as magnesium ion, zinc ion, stannous ion and the like, to obtain a metal complex. The metal ion may also be a radiolabel. Generally, the metal ion is inserted using the appropriate salts under conditions standard in the art. For example, zinc ion can be introduced by treating the compound with zinc acetate in 1:1 methylene chloride:methanol.

The compounds may also contain label, including radioisotopes, chromophores, and fluorescent labels. Radioisotope labeling is generally useful when the compounds are to be followed in vivo or used to label specific moieties. Useful cationic moieties that are radioisotopes include technetium, gallium and indium. In addition, radioisotopes of heteroatoms, such as $^{131}$I or $^{32}$P, in the molecule itself, or inclusion of $^{14}$C may be used to label the molecule.

As further described in the BPD-related patents set forth above, the compounds of the invention may be coupled, if desired, to a targeting agent which will direct the molecule to a specific tissue or organ. Such targeting agents include antibodies, receptors, receptor-ligands and the like. Linkage of the targeting agent to the compound is conducted using standard techniques. As used herein, the term "conjugated forms" refers to the compounds of formulas 1–4 when coupled optionally through a linker, to these target-specific agents.

The various forms of the compounds of the invention can be used in the photodynamic therapy techniques generally known in the art. As set forth in the Background section above, photodynamic therapy can be conducted using a plethora of protocols and for a variety of indications. In addition, compounds of this type exhibit pharmacological activity in the absence of light in some instances. Standard pharmaceutical compositions, including liposomal compositions, are used as desired in such applications.

Particularly useful in these protocols are the compounds of formulas 14–16, wherein $R^5$ is vinyl, particularly where R1 and R6 are methyl, of formula 14 or the corresponding A ring substituted form (13), again particularly where R1 and R6 are methyl, and in particular the compound B3 of Example 3 below.

Preparation of the Triacid

Central to the synthesis of the compounds of the invention is the preparation of the triacids of the compounds of formulas 1–4, i.e., wherein X and Y are OH. In this preparation, a form of the compounds of formulas 1–4 which is more highly esterified with respect to the vinyl carboxyl and the propionic carboxyl than the triacid itself is used as the starting material. Typically, the vinyl carboxyl will be in the form of an ester, typically an alkyl ester, and the propionic carboxyls may also be esterified. Alternatively, substituted hydrocarbon radical esters can be used as starting materials as can the corresponding amides.

As reactions at the propionic carboxyls are much more facile than that at the vinyl carboxyl, typical starting materials include compounds of formulas 1–4 wherein the vinyl carboxyl is an ester or an amide, while the propionic carboxyls may already be completely or partially hydrolyzed. Thus, typical starting materials would include compounds of the general formulas 1–4 wherein the vinyl carboxyl and propionic carboxyl are all in the esterified or amidated form, or those wherein the vinyl carboxyl and propionic carboxyl are all in the amide form, or the corresponding compounds in which the propionic carboxyls are completely or partially hydrolyzed. Mixed amides and esters can also be used as starting materials.

These starting materials are dissolved in an appropriate solvent, such as dimethylformamide (DMF), dimethylsulfoxide (DMSO) or tetrahydrofuran (TEF) or mixtures, and treated with a suitable base, such as sodium hydroxide, potassium hydroxide, lithium hydroxide, calcium hydroxide, barium hydroxide, chromium hydroxide or tetraalkylammonium hydroxide or any other suitable strong base. Solid, resin-based alkali reagents can also be used. Water may also be present in the reaction mixture, as may low molecular weight alcohols. Typical concentrations of base are in the range of 0.1–1M. It is preferred that the reaction take place under an oxidatively inert atmosphere such as would be provided by nitrogen, helium or argon. The temperature of the reaction mixture is in the range of 0°–60° C., but typically is conducted at room temperature. The time of reaction is that sufficient to effect hydrolysis of the vinyl carboxyls, typically 2–48 hours. This depends on the temperature at which the reaction runs, but typically, if the reaction is run at room temperature, the reaction will be complete in about 18 hours. The progress of hydrolysis can be followed chromatographically, e.g., by TLC or HPLC, so that the appropriate time period can be chosen.

The triacid reaction product often precipitates under the reaction conditions but can be redissolved by the addition of water. Preferably the product is then reprecipitated by lowering the pti to about 3–4 by using any convenient acid, usually sulfuric, nitric, hydrochloric or $CF_3SO_3H$. The precipitated triacid can be recrystallized in suitable solvents. A particularly favored solvent is wet methanol.

Once the purified crystallized product is obtained, the triacid can be treated under standard reactions conditions as set forth in Reaction Schemes 1–4 above to prepare a wide variety of photoactive agents of formulas 1–4. Conversions of the group represented by $R^5$ can be conducted with respect to any of the intermediates or with respect to starting materials and products.

The following examples are intended to illustrate but not to limit the invention.

EXAMPLE 1

Preparation of Triacid of Formula 6

1.0 g (1.37 mM) of the tetraester obtained from the B-ring Diels-Alder adduct to protoporphyrin IX—i.e., the compound of formula 2 wherein $R^1$ is Me, Y and X are —OMe, n is 2, and $R^5$ is vinyl, was added to a suspension of LiOH (1.0 g, 41 mM) in 50 ml of tetrahydrofuran, 10 ml of methanol and 5.0 ml of water which had been degassed by stirring under nitrogen for 1 hour. The reaction was stirred for 18 hours under a slow nitrogen stream. It was monitored by silica gel TLC using dichloromethane/methanol as a developing solvent. The reaction mixture was worked up by first adding 100 ml of water and then bringing the pH down to 3–4 with 5% HCl. The solid was filtered and washed with water which had been buffered with acetic acid to pH 3.5. The solid triacid of formula 6 was recrystallized from wet methanol to give 770 mg (82%) yield. The triacid decomposes upon melting. Structure was confirmed by C/H and N analysis along with NMR. The NMR showed the loss of the methyl ester resonance from the propionic acid side chains as well as of the down-field resonance assigned to the ester on the vinyl group. To verify structure, the triacid of formula 6 was treated with diazomethane to regenerate the starting material.

EXAMPLE 2

Preparation of Ethylene Glycol Triester 50 mg (72 $\mu$M) of the triacid obtained in Example 1 were dissolved in dry dimethyl formamide (MF) (2 ml) and activated with benzotriazol-1-yl N, N, N',N' tetramethyl uronium tetrafluoroborate (BTTU) (Aldrich) (100 mg, 310 $\mu$M) in the presence of triethylamine (50 $\mu$l). BTTU is the carboxyl activating agent of the formula

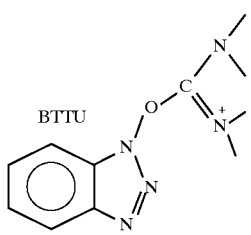

BTTU

The reaction was stirred for six hours and then 250 μl of ethylene glycol and then 20 μl of DBU were added. After 30 minutes, the reaction was then added to a stirred solution of 20 ml of dichloromethane and 10 ml water. The organic layer was isolated and washed three more times with 5 ml water at each wash. The solvent was removed, leaving a dark green oil. The product, 27 mg of the ethylene glycol triester (38%) was isolated from a preparative thin-layer chromatographic plate eluting with 5% methanol in choromethane.

EXAMPLE 3

Preparation of B3

To 200 mg (0.289 mmoles) of the triacid prepared in Example 1 in 10.0 ml of methanol was added ~100 microliter (1 mmoles) of sulfuric acid. The reaction was quenched after 2 hours by the addition of 10 ml of 5% ammonium acetate and 20 ml of dichloromethane. The organic layer was washed twice with water. To the product solution was added 10 ml acetonitrile. The solvent was removed by rotary evaporation to give a dark green powder. The product, B3 was crystallized from methanol/chloroform to give 140 mg (67%) of dark green solid after drying at 60 C. under vacuum for 4 hours.

The product decomposes on melting. Structure was confirmed by C/H and N analysis, Mass Spectral Analysis along with proton NMR, as of formula 14 wherein $R^5$ is vinyl and $R^1$ and $R^6$ are methyl.

EXAMPLE 4

Photosensitization of Cells in Vitro

Figure 2:
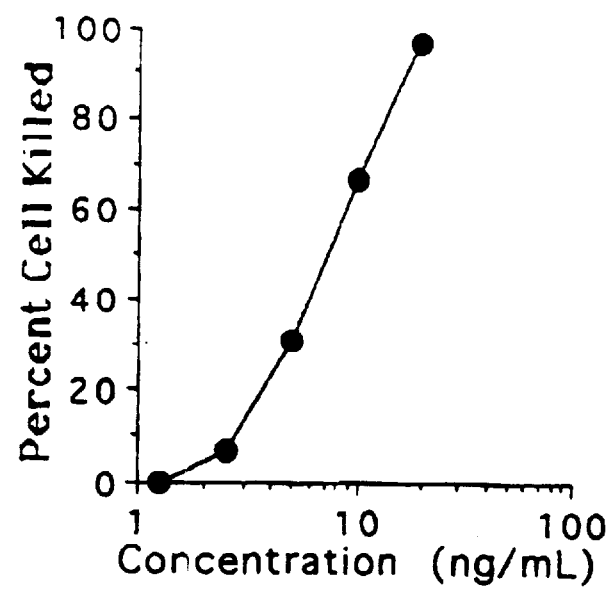
FIGS. 2A and 2B show the photosensitization of L1210 cells in vitro by B3 as a function of concentration.
Figure 2:
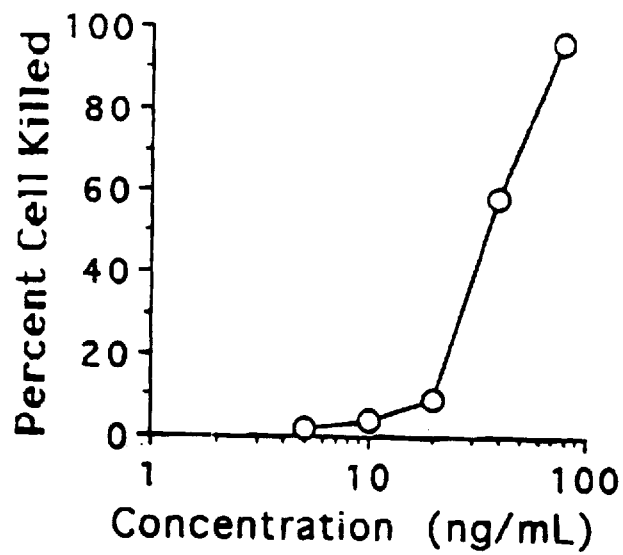

Murine leukemia cells (L1210) were incubated in suitable buffer with and without serum in various amounts of the drug B3 for 1 hour. After removal of the drug, the cells were exposed to broad spectrum light at 9 j/cm$^2$. Cell viability was determined 20 hours later by the MTT colorimetric assay. Results are presented in FIGS. 2A and 2B as % cell kill for cells exposed to light only. The $LD_{50}$ (dose causing 50% cell kill) was 7 ng/ml in the absence of, and 35 ng/ml in the presence of, 10% serum. Thus, B3 is a very potent photosensitizer of cells and maintains this property in the presence of serum.

EXAMPLE 5

Cellular Pharmacokinetics

Uptake of B3 by cells in vitro: L1210 cells (5×10$^6$/vial) were incubated in the presence of 10% serum with B3 at 3 μg/ml for times up to 100 minutes. At various times during incubation, duplicate vials were pulled out and the cells, following washing, were lysed and the amount of B3 in the extract determined by fluorescence in the presence of 1% Triton X-100.

Release/retention of B3 by cells in vitro: L1210 cells were incubated for 1 hour with B3 at 3 μg/ml in the presence of 10% serum, then washed and placed in drug-free medium containing 10% serum. At various times duplicate aliquots were evaluated for cell content of B3 as described above.

Figure 3:
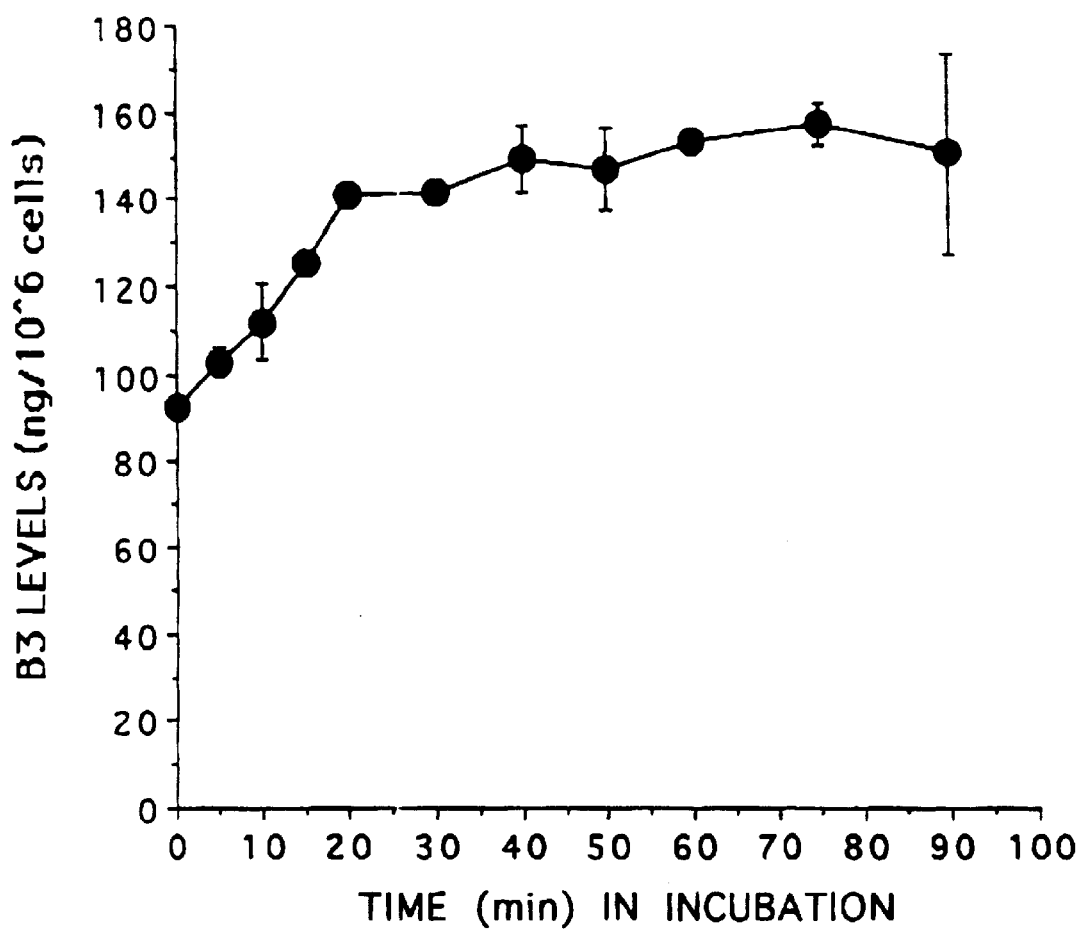
FIG. 3 shows the time course of uptake of B3 by L1210 cells.
Figure 4:
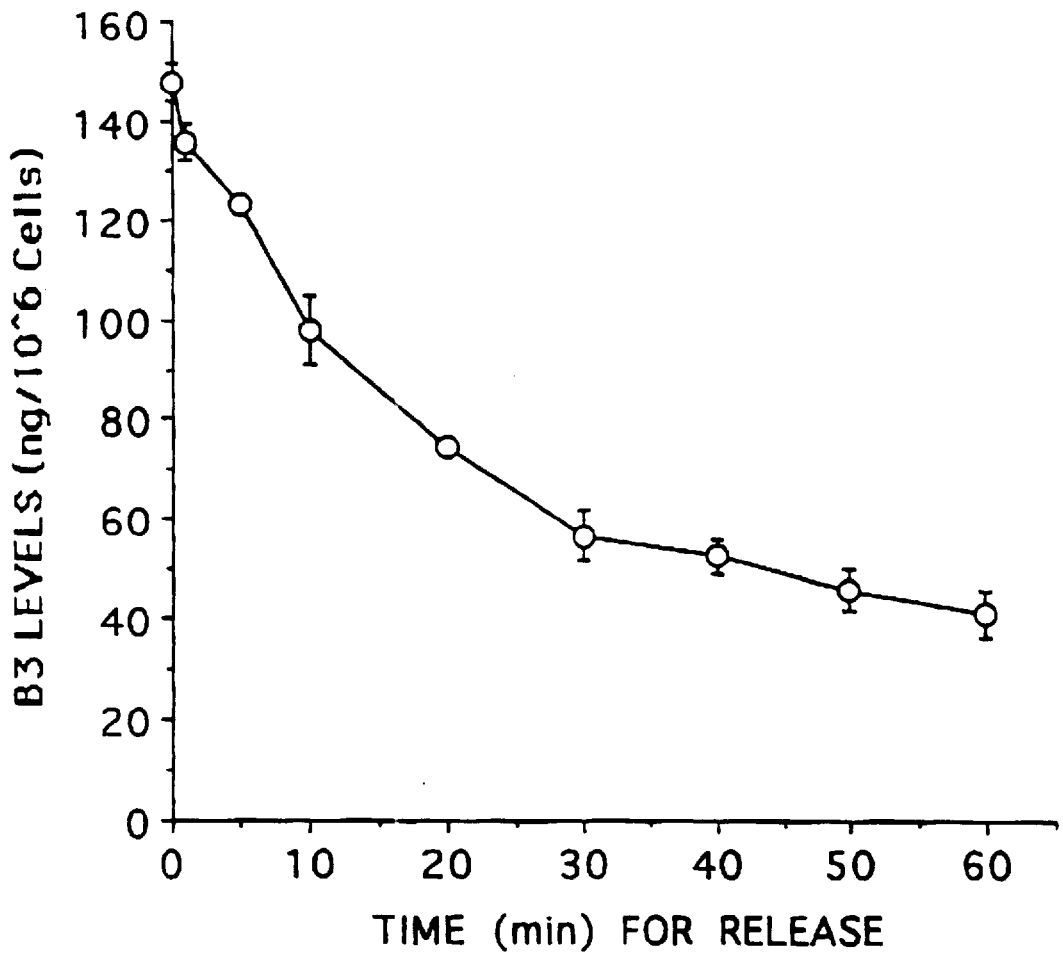
FIG. 4 shows the kinetics of release of B3 from L1210 cells after 1 hour incubation.

The results presented in FIGS. 3 and 4 indicate that B3 has very rapid pharmacokinetics in vitro. The compound enters cells rapidly, reaching maximum concentrations within 20 min. After removal of the B3 from the culture medium, release is rapid and almost complete after 30 min. Based on experience with other drugs, B3 is expected to have very rapid pharmacokinetics in vivo, thus avoiding prolonged skin photosensitivity.

EXAMPLE 6

Tissue Distribution and Clearance in Vivo

Mice (normal, healthy and M1-tumor-bearing) were injected intravenously at 4 mg/kg with B3 formulated in aqueous solution containing DMSO. At various times post B3 administration, the animals were sacrificed and B3 content in various tissues was determined in tissue extracts by fluorescence as described above.

Figure 5:
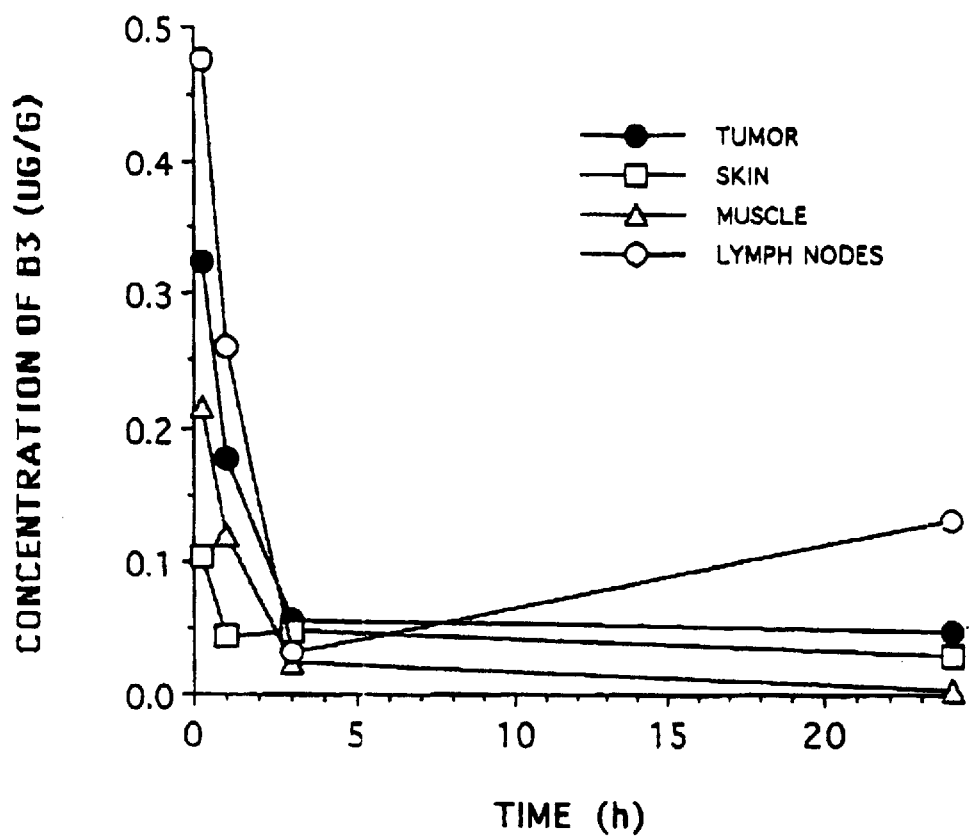
FIG. 5 shows the biodistribution of B3 in mouse tissues.

The results are shown in FIG. 5. The drug was cleared from tissues tested after about 5 minutes. Thus, B3 has very rapid pharmacokinetics in vivo, confirming the expectation that prolonged skin hypersensitivity will not result when the drug is used therapeutically.

EXAMPLE 7

Selectivity in Vivo

Biodistribution data of B3 (tumor:tissue ratios) obtained in M1 (rhabdomyosarcoma) tumor-bearing mice were also evaluated at various times. Within the first hour post intravenous administration of 4 mg/kg B3, tumor:tissue ratios for the muscle and skin were 1.5–2.0 and 3.1–3.9, respectively. Lymph nodes gave ratios of 0.7. The results indicate preferential accumulation of B3 in tumor and other rapidly proliferating tissues (lymph nodes) in contrast to normal, nonproliferating tissues. Since this preferential accumulation was observed shortly after B3 administration, this photosensitizer can be activated with light shortly after its injection, which is convenient in clinical use.

We claim:

1. A compound of the formula

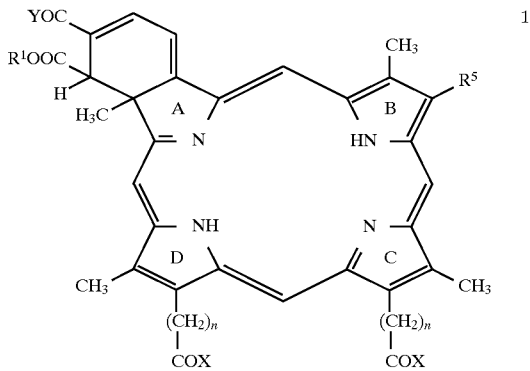

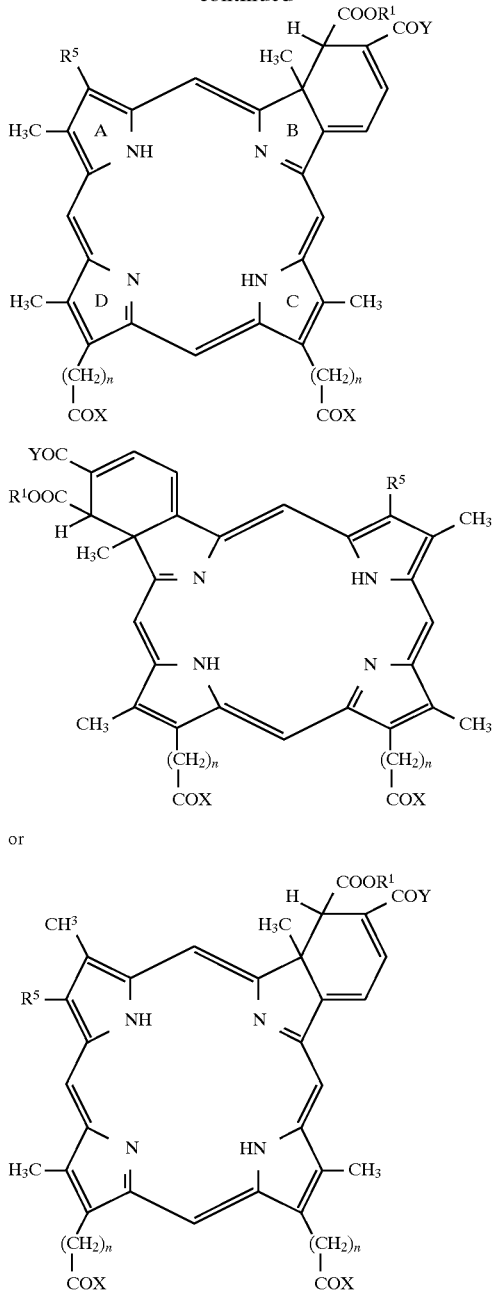

or and salts and/or metallated and/or labeled and/or conjugated forms thereof wherein $R^1$ is alkyl (1-6C);

Y is —OH or —$NR^2_2$ or —$NHNR^2_2$ wherein each $R^2$ is independently H or a substituted or unsubstituted hydrocarbon radical of 1-10C, or wherein both $R^2$ taken together provide a cyclic or multicyclic amine of 1-20C; or is —$OR^3$ wherein $R^3$ is alkyl (1-10C) substituted with at least one heteroatom-containing substituent;

n is an integer of 0–6 each X is independently —OH; or —$OR^4$, wherein $R^4$ is an unsubstituted hydrocarbon radical of 1-10C; or is —$NR^2_2$ or —$NHNR^2_2$ wherein $R^2$ is defined as above; or is —$OR^3$ wherein $R^3$ is as defined above; and $R^5$ is vinyl or a derivative thereof.

2. The compound of claim 1 wherein n is 2.

3. The compound of claim 1 wherein $R^5$ is vinyl, —CHOR', —CHO, —COOR', —CH(OR')CH$_3$, —CH(OR')CH$_2$OR', —CH(SR')CH$_3$, —CH(NR')$_2$CH$_3$, —CH(CN)CH$_3$, —CH(COOR')CH$_3$, —CH(OOCR')CH$_3$, —CH(NR'COR')CH$_3$, —CH(CONR'$_2$)CH$_3$, —CH(halo)CH$_3$, or —CH(halo)CH$_2$(halo) wherein R' is H, or a hydrocarbon radical (1-6C) optionally substituted with a heteroatom-containing substituent or wherein $R^5$ is an organic group of less than 12C resulting from direct or indirect derivatization of the vinyl group, or wherein $R^5$ comprises a group containing 1–3 tetrapyrrole-type nuclei.

4. The compound of claim 2 wherein $R^5$ is vinyl, —CHOR', —CHO, —COOR', —CH(OR')CH$_3$, —CH(OR')CH$_2$OR∝, —CH(SR')CH$_3$, —CH(NR')$_2$CH$_3$, —CH(CN)CH$_3$, —CH(COOR')CH$_3$, —CH(OOCR')CH$_3$, —CH(NR'COR')CH$_3$, —CH(CONR'$_2$)CH$_3$, —CH(halo)CH$_3$, or —CH(halo)CH$_2$(halo) wherein R' is H, or a hydrocarbon radical (1-6C) optionally substituted with a heteroatom-containing substituent.

5. The compound of claim 4 wherein $R^5$ is vinyl.

6. The compound of claim 1 wherein Y and both X are —OH.

7. The compound of claim 2 wherein Y and both X are —OH.

8. The compound of claim 7 which is the "triacid" of the formula

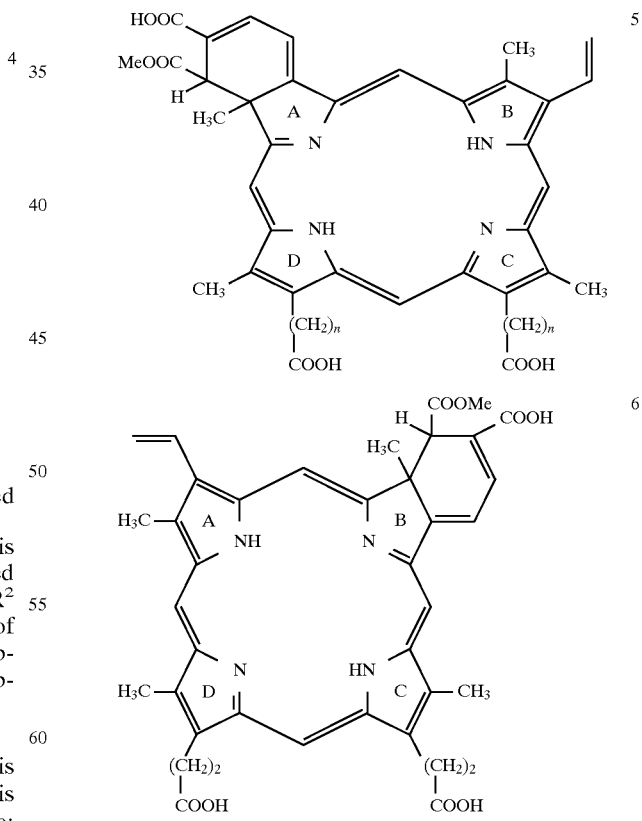

-continued

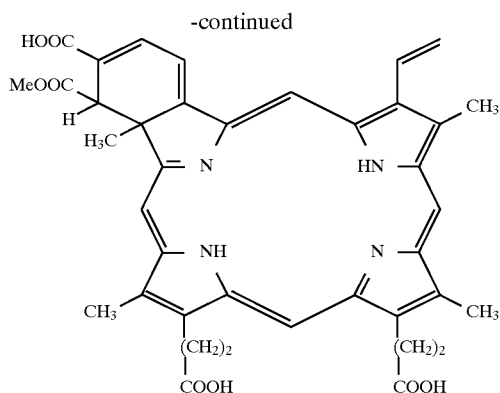

7

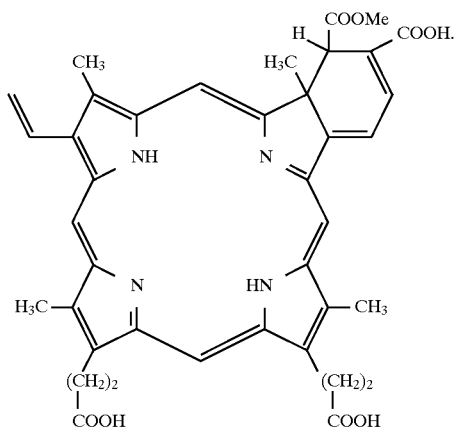

8 or

9. The compound of claim 1 wherein Y is —$NR^2_2$.
10. The compound of claim 2 wherein Y is —$NR^2_2$.
11. The compound of claim 3 wherein Y is —$NR^2_2$.
12. The compound of claim 4 wherein Y is —$NR^2_2$.
13. The compound of claim 9 wherein each —$NR^2_2$ independently comprises methyl, ethyl, propyl, butyl, isobutyl, hexyl, hydroxyalkyl (1-6C), cyclopentyl, cyclopentadienyl, furyl, thienyl, pyrrolyl, isopyrrolyl, pyridyl, pyrazolyl, indolyl, isoindolyl, imidazolyl, isoimidazolyl, triazolyl, furazanyl, isoxazolyl, oxazolyl, thiazolyl, isothiazolyl, oxadiazolyl, oxatriazolyl, dioxazolyl, phenyl, cyclohexyl, pyranyl, dioxinyl, pyridinyl, pyridazinyl, pyrimidinyl, pyrazinyl, piperazinyl, indolyzinyl, pyrrolidinyl, triazinyl, oxazinyl, isoxazinyl, oxathiazinyl, oxadiazinyl, morpholinyl, azepinyl, oxepinyl, thiepinyl, diazepinyl, indenyl, isoindenyl, benzofuranyl, isobenzofuranyl, thionaphthenyl, isothionaphthenyl, indolenyl, isobenzazolyl, pyrano-pyrrolyl, indazolyl, isoindazolyl, indoxazinyl, benzoxazolyl, chromenyl, anthanyl, naphthyl, tetralinyl, decalinyl, benzothienyl, benzyopyranyl, coumarinyl, cinnolinyl, benzopyronyl, quinolinyl, isoquinolinyl, benzodiazinyl, quinolyl, isoquinolyl, quinazolinyl, quinolizinyl, quinoxalinyl, naphthyridinyl, pyrido-pyridinyl, benzoxazinyl, benzisoxazinyl, purinyl, phthalazinyl, naphthyridinyl, pteridinyl, or benzyl.
14. The compound of claim 9 wherein both X are —$NR^2_2$.
15. The compound of claim 13 wherein both X are —$NR^2_2$.
16. The compound of claim 1 wherein both X and Y are —$OCH_2CH_2OH$.
17. The compound of claim 5 wherein both X and Y are —$OCH_2CH_2OH$.
18. The compound of claim 5 wherein Y is OH, both X are —$OR^6$, wherein $R^6$ is lower alkyl (1-4C).
19. The compound of claim 18 wherein $R^6$ is methyl.
20. The compound of claim 19 wherein $R^1$ is methyl.
21. The compound of claim 20 which is of formula 13 or 14.
22. A method to prepare a product compound of the formula

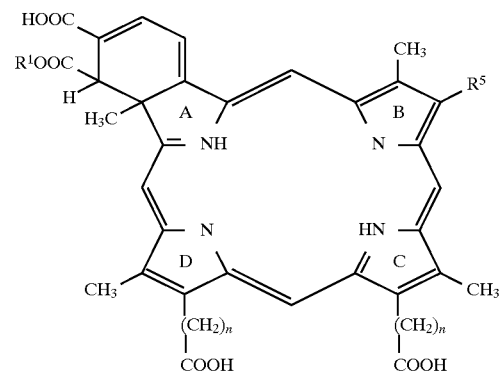

9

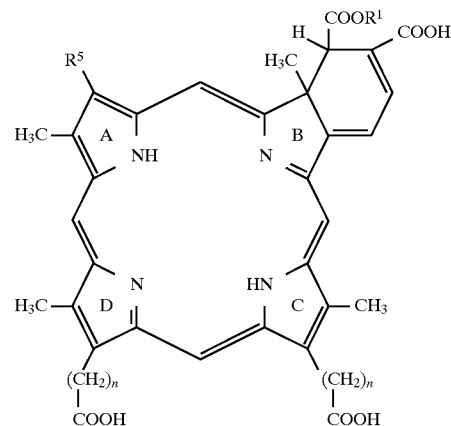

10

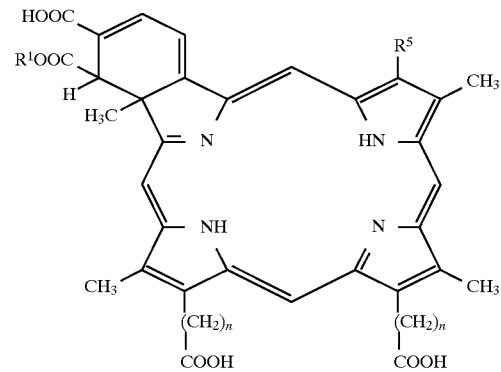

11 or

-continued

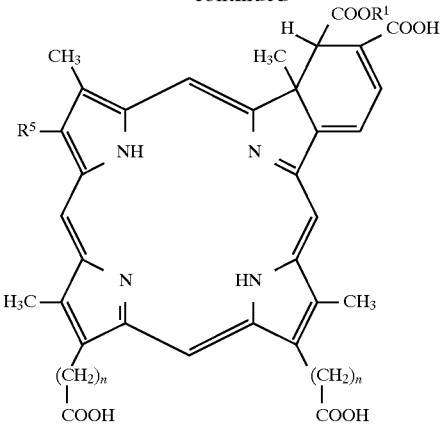
12 and the salts and/or metallated and/or labeled and/or conjugated forms thereof;
wherein $R^1$ is alkyl (1-6C);
n is an integer of 1–6; and
wherein $R^5$ is vinyl or a derivative thereof,
which method comprises treating a more highly esterified form of said product compound or the salt, metallated form, labeled form or conjugated form thereof,
with a base and solvent for a time sufficient to result in deesterification so as to obtain the product compound.

23. The method of claim 22 wherein said treating is conducted in an inert atmosphere that prevents oxidation.

24. The method of claim 22 wherein said base is sodium hydroxide, potassium hydroxide, lithium hydroxide, calcium hydroxide, barium hydroxide, chromium hydroxide, or tetraalkyl ammonium hydroxide.

25. The method of claim 23 wherein said base is sodium hydroxide, potassium hydroxide, lithium hydroxide, calcium hydroxide, barium hydroxide, chromium hydroxide, or tetraalkyl ammonium hydroxide.

26. The method of claim 22 wherein the solvent is DMSO, low molecular weight alcohol, DMF, THF or water or mixtures thereof.

27. The method of claim 23 wherein the solvent is DMSO, low molecular weight alcohol, DMF, THF or water or mixtures thereof.

28. The method of claim 23 wherein said inert atmosphere is provided by nitrogen, helium or argon gas.

29. The method of claim 22 wherein said treating is conducted at a temperature of about 0°–60° C.

30. The method of claim 23 wherein said treating is conducted at a temperature of about 0°–60° C.

31. The method of claim 22 wherein said treating is conducted at room temperature for about 2–48 hours.

32. The method of claim 23 wherein said treating is conducted at room temperature for about 2–48 hours.

33. The method of claim 22 which further comprises dissolving any product compound or its salt, metallated form, labeled form or conjugated form in water and adding sufficient acid to precipitate said product compound.

34. The method of claim 23 which further comprises dissolving any product compound or its salt, metallated form, labeled form or conjugated form in water and adding sufficient acid to precipitate said product compound.

35. A method to prepare a compound of formulas 1–4 or salts or metallated or labeled or conjugated forms thereof, wherein $R^1$ is alkyl (1-6C); Y and both X are —$OR^3$ or —$NR^2_2$; n is an integer of 0–6; and $R^5$ is vinyl or a derivative thereof; which method comprises treating a carboxyl-activated form of a starting compound of the formula

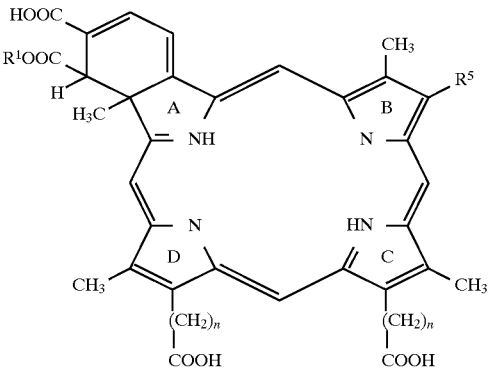
9

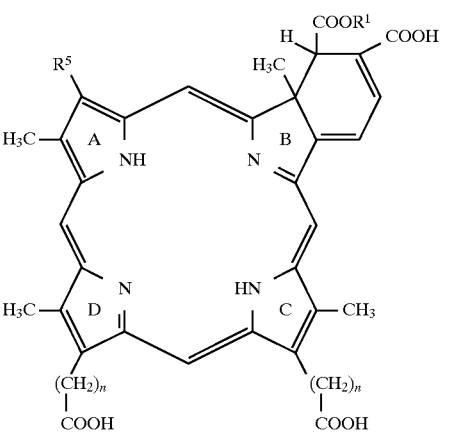
10

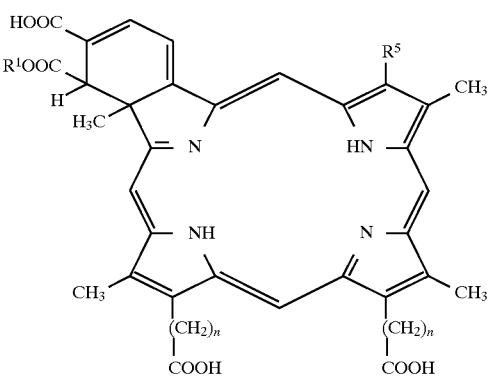
11 or

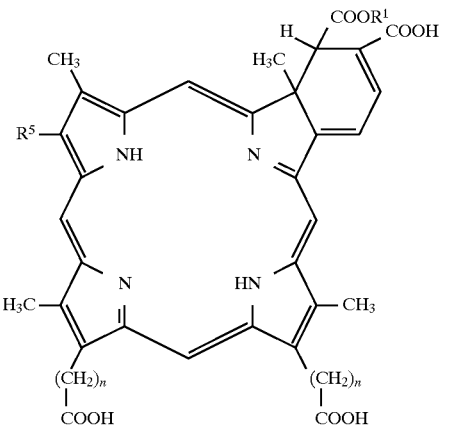
12 and the salts and/or metallated and/or labeled and/or conjugated forms thereof;

wherein $R^1$ is alkyl (1-6C);

n is an integer of 1–6; and wherein $R^5$ is vinyl or a derivative thereof, with $R^3OH$ or $HNR^2_2$ under conditions which are sufficient to form a compound of formulas 1–4 or the metallated or labeled or conjugated form thereof wherein Y and both X are either —$OR^3$ or $NR^2_2$.

36. The method of claim 35 wherein the activated carboxyl is obtained by treating free carboxyl groups of said starting compound with an activating agent.

37. The method of claim 36 wherein the activating agent is TSTU or BTTU.

38. The method of claim 35 wherein Y and both X are —$OR^3$.

39. The method of claim 38 wherein —$OR^3$ is —$OCH_2CH_2OH$ and —$R^3OH$ is ethylene glycol.

40. A pharmaceutical composition comprising the compound of claim 1 in admixture with a pharmaceutically acceptable excipient.

41. An improved method to conduct PDT wherein the improvement comprises employing the compound of claim 1 as a photoactive agent.

42. A pharmaceutical composition comprising the compound of claim 18 in admixture with a pharmaceutically acceptable excipient.

43. An improved method to conduct PDT wherein the improvement comprises employing the compound of claim 18 as a photoactive agent.

* * * * *

UNITED STATES PATENT AND TRADEMARK OFFICE
CERTIFICATE OF CORRECTION

PATENT NO. : 5,880,145
DATED : March 9, 1999
INVENTOR(S) : Ethan D. STERNBERG; et al.

It is certified that error appears in the above-identified patent and that said Letters Patent is hereby corrected as shown below:

ON THE TITLE PAGE:

Line [54] "CLASS OF BENZOPORPHYRIN DERIVATIVE PHOTOACTIVE COMPOUNDS" should read --A NEW CLASS OF BENZOPORPHYRIN DERIVATIVE PHOTOACTIVE COMPOUNDS--.

Signed and Sealed this

Fourteenth Day of September, 1999

*Attest:*

Q. TODD DICKINSON

*Attesting Officer*  Acting Commissioner of Patents and Trademarks